United States Patent
Mattke et al.

(10) Patent No.: US 8,791,291 B2
(45) Date of Patent: Jul. 29, 2014

(54) PROCESS FOR PREPARING ISOCYANATES BY PHOSGENATION OF THE CORRESPONDING AMINES IN THE GAS PHASE

(71) Applicants: Torsten Mattke, Freinsheim (DE); Carsten Knöesche, Niederkirchen (DE); Vanessa Simone Lehr, Mannheim (DE)

(72) Inventors: Torsten Mattke, Freinsheim (DE); Carsten Knöesche, Niederkirchen (DE); Vanessa Simone Lehr, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/687,670

(22) Filed: Nov. 28, 2012

(65) Prior Publication Data

US 2013/0137892 A1 May 30, 2013

Related U.S. Application Data

(60) Provisional application No. 61/564,319, filed on Nov. 29, 2011.

(51) Int. Cl.
*C07C 263/00* (2006.01)

(52) U.S. Cl.
USPC .......................................................... 560/347

(58) Field of Classification Search
None
See application file for complete search history.

(56) References Cited

U.S. PATENT DOCUMENTS

| | | | |
|---|---|---|---|
| 2011/0213177 A1* | 9/2011 | Mattke et al. ................. | 560/347 |
| 2011/0230676 A1 | 9/2011 | Lehr et al. | |
| 2012/0095255 A1 | 4/2012 | Mattke et al. | |
| 2012/0251435 A1 | 10/2012 | Lehr et al. | |
| 2012/0253063 A1 | 10/2012 | Mattke et al. | |

FOREIGN PATENT DOCUMENTS

| WO | WO 2011/067369 A1 | 6/2011 |
|---|---|---|
| WO | WO 2011/104264 A1 | 9/2011 |
| WO | WO 2011/113737 A1 | 9/2011 |
| WO | WO 2012/049158 A1 | 4/2012 |
| WO | WO 2012/130788 A | 10/2012 |
| WO | WO 2013/029918 A1 | 3/2013 |

OTHER PUBLICATIONS

U.S. Appl. No. 13/587,378, filed Aug. 16, 2012, Torsten Mattke, et al.
U.S. Appl. No. 13/661,652, filed Oct. 26, 2012, Julia Leschinski, et al.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

A process for preparing isocyanates by phosgenation of the corresponding amines in a fluidized-bed reactor (R), wherein a gas stream (1) comprising the phosgene is used as fluidizing gas and keeps an inert solid in suspension and a liquid stream (2) comprising the amine is fed into the fluidized bed, with the amine vaporizing partially or completely and reacting with the phosgene to give a reaction gas mixture which comprises the corresponding isocyanate and is taken off from the fluidized-bed reactor (R) is proposed.

18 Claims, 2 Drawing Sheets

Figure 1:
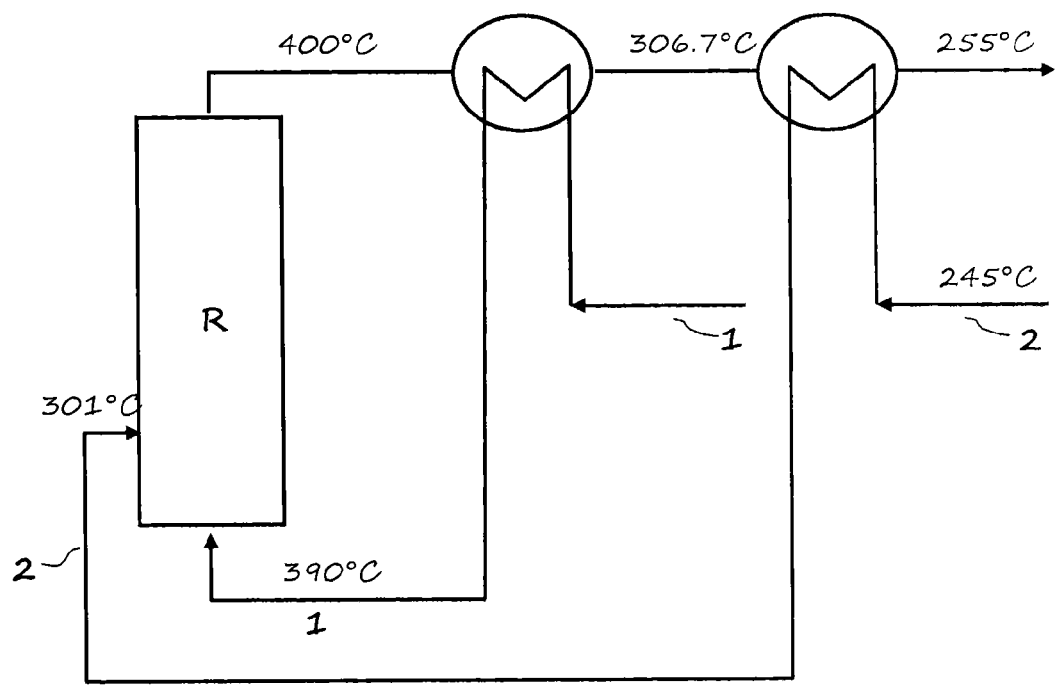

PROCESS FOR PREPARING ISOCYANATES BY PHOSGENATION OF THE CORRESPONDING AMINES IN THE GAS PHASE

The invention relates to a process for preparing isocyanates by phosgenation of the corresponding amines.

Phosgenation is the process which is by far the most widely used in industry for the synthesis of isocyanates. Isocyanates, in particular diisocyanates, are predominantly used as starting materials in the polyurethane industry.

In the known processes, the phosgenation is generally carried out in the liquid phase.

More recent processes are carried out in the gas phase since gas-phase phosgenation has a number of advantages over liquid-phase phosgenation:

In liquid-phase phosgenation, amine hydrochlorides are precipitated as solids as a result of the reaction of the amines used with the hydrogen chloride eliminated in the phosgenation. Although the amine hydrochlorides also react further with phosgene to form the target product isocyanate, this is a slow reaction involving a solid and leads to increased occurrence of secondary reactions, especially the reaction of amine hydrochlorides with the target product isocyanate to form ureas.

On the other hand, in gas-phase phosgenation, the amine to amine hydrochloride equilibrium is heavily on the amine side, so that a significantly smaller amount of by-products is formed and the yields are correspondingly higher. In addition, the holdup of toxic phosgene is lower in gas-phase phosgenation than in liquid-phase phosgenation.

However, gas-phase phosgenation is significantly more demanding in terms of process engineering than liquid-phase phosgenation: in particular, the risk of decomposition of the amine and of the isocyanate formed is very great, so that the amine has to be vaporized very quickly. Very large specific surface areas are required for this purpose. In addition, very short, defined residence times in the high-temperature region have to be ensured during the reaction and the product mixture has to be cooled very quickly after the reaction.

It was an object of the invention to provide a process for preparing isocyanates by phosgenation of the corresponding amines in the gas phase which overcomes the above challenges.

The object is achieved by a process for preparing isocyanates by phosgenation of the corresponding amines in a fluidized-bed reactor, wherein a gas stream comprising the phosgene is used as fluidizing gas and keeps an inert solid in suspension and a liquid stream comprising the amine is fed into the fluidized bed, with the amine vaporizing partially or completely and reacting with the phosgene to give a reaction gas mixture which comprises the corresponding isocyanate and is taken off from the fluidized-bed reactor.

As a result of the starting material amine being, according to the invention, sprayed in the liquid state into the fluidized bed which has been heated by the heat of reaction of the phosgenation reaction, the amine is vaporized and superheated very quickly so that the risk of deposits on the inert solid forming the fluidized bed is low. The inert solid can be discharged and any deposits can be burnt off. Overall, this is a very robust system which does not suffer from the risk of being clogged by deposits.

Since the process utilizes the heat of reaction of the phosgenation reaction itself, the very expensive high-temperature energy which in previously known processes was destroyed by quenching the reaction mixture from the gas-phase phosgenation is utilized where it is generated in order to bring the starting materials to the operating temperature of the gas-phase phosgenation.

In addition, the corresponding heat exchangers are also saved or can be made smaller.

The heat of reaction liberated in the gas-phase phosgenation is transported by the circulations in the fluidized bed into regions for heating, vaporization or superheating of the feed streams.

A further advantage of the way in which the process of the invention is carried out in a fluidized bed is that an adiabatic temperature increase of the reaction mixture and thus high exit temperatures of the reaction mixture can be avoided.

The fluidized-bed reactor is preferably a rotationally symmetrical apparatus having a vertical longitudinal axis. The fluidized-bed reactor is more preferably a predominantly cylindrical apparatus.

The phosgene-comprising gas stream which both comprises the starting material phosgene and is used as fluidizing gas in the fluidized-bed reactor is preferably heated to a temperature which is at least 5° C. greater than the vaporization temperature of the amine under the operating conditions in the fluidized-bed reactor before being fed into the fluidized-bed reactor.

The phosgene-comprising gas stream preferably comprises from 50 to 100% by weight of phosgene, based on the total weight of the phosgene-comprising gas stream, preferably from 75 to 100% by weight of phosgene, based on the total weight of the phosgene-comprising gas stream, more preferably from 90 to 99.9% by weight of phosgene, based on the total weight of the phosgene-comprising gas stream.

The amine-comprising liquid stream which is fed into the fluidized bed is preheated to a temperature which is at least 1° C. below, preferably at least 5° C. below, the boiling point of the amine under the operating conditions in the fluidized-bed reactor, preferably directly before being fed into the fluidized bed.

The amine-comprising liquid stream preferably comprises from 50 to 100% by weight of amine, based on the total weight of the amine-comprising liquid stream, more preferably from 70 to 100% by weight of amine, based on the total weight of the amine-comprising liquid stream, in particular from 90 to 99.99% by weight of amine, based on the total weight of the amine-comprising liquid stream.

Amines which are used in the process of the invention for the reaction to form the corresponding isocyanates are ones in the case of which the amine, the corresponding intermediates and the corresponding isocyanates are present in gaseous form under the reaction conditions selected. Preference is given to amines which decompose to an extent of not more than 2 mol %, particularly preferably not more than 1 mol % and very particularly preferably not more than 0.5 mol %, during the duration of the reaction under the reaction conditions. Particularly suitable amines here are amines, in particular diamines, based on (cyclo)aliphatic hydrocarbons having from 2 to 18 carbon atoms. Examples are 1,6-diaminohexane, 1,5-diaminopentane, 1,3-bis(aminomethyl)cyclohexane, 1-amino-3,3,5-trimethyl-5-aminomethylcyclohexane (IPDA) and 4,4-diaminodicyclohexylmethane. Preference is given to using 1,6-diaminohexane (hexamethylenediamine, HDA).

In the process of the invention, it is likewise possible to use aromatic amines which can be brought into the gas phase without significant decomposition. Examples of preferred aromatic amines are tolylenediamine (TDA), as 2, 4 or 2,6 isomer or as a mixture thereof, for example as from 80:20 to 65:35 (mol/mol) mixture, diaminobenzene, 2,6-xylidine, naphthyldiamine (NDA) and 2,4'- or 4,4'-methylenedi(phenylamine) (MDA) or isomer mixtures thereof. Among these, preference is given to the diamines and particular preference is given to 2,4- and/or 2,6-TDA or 2,4'- and/or 4,4'-MDA.

To prepare monoisocyanates, it is likewise possible to use aliphatic, cycloaliphatic or aromatic amines, usually monoamines. Aniline is particularly preferred as aromatic monoamine.

Furthermore, triamines or higher amines can also be used.

It is desirable in the gas-phase phosgenation for the compounds occurring during the course of the reaction, i.e. starting materials (amine and phosgene), intermediates (in particular the carbamoyl chlorides and amine hydrochlorides formed as intermediates), end products (diisocyanates) and also any inert compounds introduced, to remain in the gas phase under the reaction conditions. Should these or other components precipitate from the gas phase, for example on the reactor wall or other components of the apparatus, these deposits can change either heat transfer or flow through the affected components in an undesirable way. This applies particularly to amine hydrochlorides which are formed from free amino groups and hydrogen chloride, since these precipitate easily and can be revaporized only with difficulty.

To avoid the formation of by-products, phosgene is preferably introduced in excess. To introduce only the proportion of amines necessary for the reaction, it is possible to mix the amine with an inert gas. The amount of amine introduced at a given geometry of the feed openings for the amine and the phosgene can be set via the proportion of inert gas in the amine. Inert media which can be added are those which are present in gaseous form in the reaction space and do not react with the compounds occurring in the course of the reaction. As inert medium, it is possible to use, for example, nitrogen, noble gases such as helium or argon, aromatics such as chlorobenzene, o-dichlorobenzene, trichlorobenzene, toluene, xylene, chloronaphthalene, decahydronaphthalene, carbon dioxide or carbon monoxide. Preference is given to using nitrogen and/or chlorobenzene as inert medium.

However, it is also possible, as an alternative, to mix an inert medium, preferably nitrogen, into the phosgene, for example in order to avoid an excessively large excess of phosgene.

In general, the inert medium is added in such an amount that the ratio of the gas volumes of inert medium to amine or to phosgene is from <0.0001 to 30, preferably from <0.01 to 15 and particularly preferably from <0.1 to 5.

In an advantageous embodiment, the process is carried out so that a mixture comprising the reaction gas mixture and the inert solid flows out of the fluidized-bed reactor in the upper region of the reactor and is passed to a separation.

The separation into the reaction gas mixture and the inert solid is preferably carried out in one or more apparatuses selected from the group consisting of cyclones and filters.

Preferably from 50 to 100%, more preferably from 75 to 100%, particularly preferably from 90 to 100%, of the amine groups used have been reacted in the reaction gas mixture which is separated off.

The reaction gas mixture is advantageously fed to a subsequent residence time reactor to achieve complete reaction of the amine groups.

The reaction gas mixture can also advantageously be cooled in one or more stages by direct or indirect heat input and a liquid phase may be optionally condensed out during cooling.

The solid which has been separated off can advantageously be partly or completely recirculated to the lower part of the fluidized bed.

The solid is preferably worked up partly or completely, in particular in a second fluidized bed, and the worked up solid is preferably partly or completely recycled to the fluidized-bed reactor. The work-up of the solid is particularly preferably effected essentially by burning-off of carbon-comprising deposits on the solid.

The inert solid is preferably a material which is inert toward all reactants and reaction products, preferably an inorganic material, particularly preferably $SiO_2$ or $Al_2O_3$, in particular $\alpha$-$Al_2O_3$.

The average particle size of the inert solid is, in particular, in the range from 20 to 2000 μm, preferably in the range from 20 μm to 500 μm and particularly preferably in the range from 50 μm to 150 μm.

The liquid stream comprising the amine is, in particular, fed into the fluidized bed by means of one or more nozzles which are configured as one-fluid or two-fluid nozzles, preferably as two-fluid nozzles, with the atomization gas in the case of two-fluid nozzles preferably being a phosgene-comprising gas, more preferably superheated amine, an inert gas or mixtures thereof.

The two-fluid nozzles in the case of a phosgene-comprising gas as atomization gas are preferably configured as externally mixing.

When two or more nozzles are used for feeding in the liquid stream comprising the amine, these can advantageously be distributed uniformly over the cross section.

The invention is illustrated below with the aid of drawings and examples.

Figure 2:
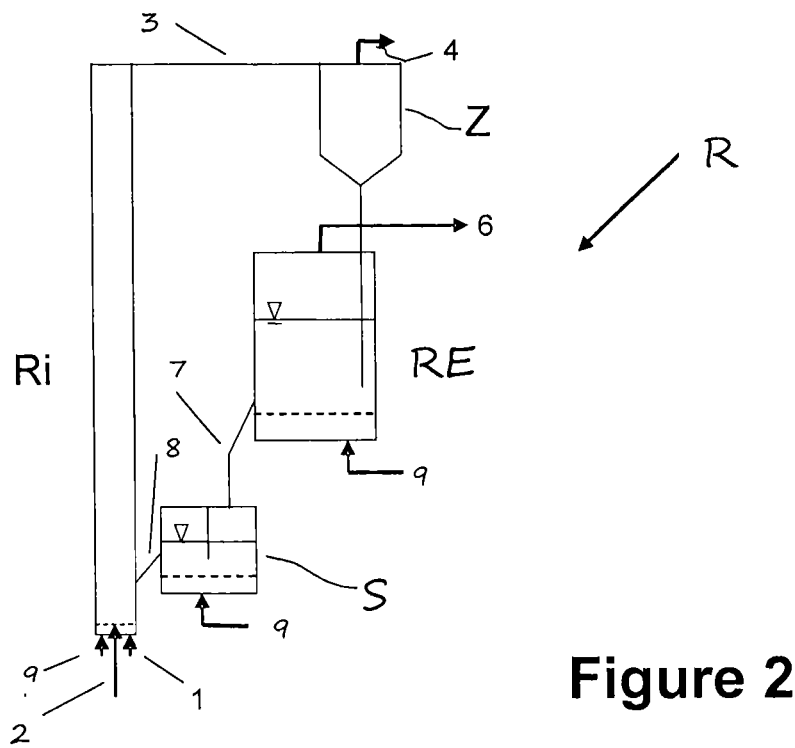
Figure 3:
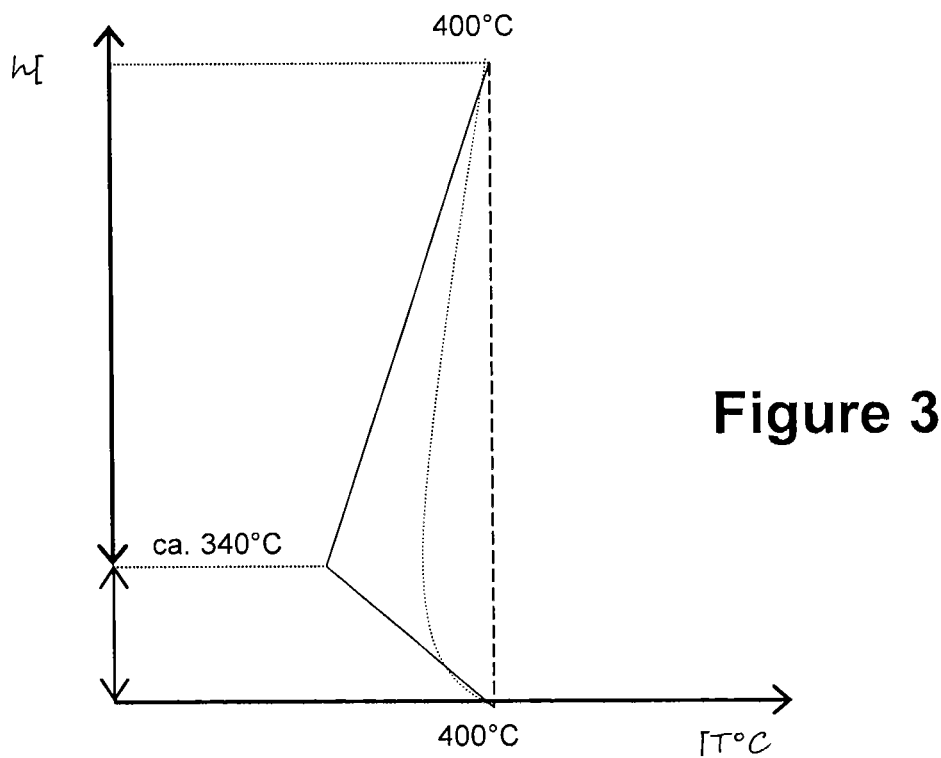

In detail:

FIG. 1 shows a process scheme for a preferred way of carrying out the process with heat integration, FIG. 2 shows a further preferred embodiment with a circulating fluidized bed set-up and FIG. 3 schematically shows the temperature profile in the riser for an example in a circulating fluidized bed set-up corresponding to FIG. 2.

In the figures, identical reference symbols denote identical or corresponding features.

FIG. 1 shows a process scheme for a preferred way of carrying out the process with heat integration. A phosgene-comprising gas stream 1 which has been preheated to 390° C. and, for example, a tolylenediamine-comprising stream 2 which has been heated by means of 40 bar steam to 245° C. and subsequently by means of the reaction mixture of the phosgenation to 301° C. and remains in the liquid state and is subsequently sprayed into the fluidized-bed reactor are introduced into a schematically depicted fluidized-bed reactor R. The vaporization of the tolylenediamine and the reaction thereof with the phosgene occur at a temperature of about 400° C. in the fluidized-bed reactor. Here, the heat of reaction liberated corresponds to the heat required for vaporization and heating of the starting materials.

FIG. 2 shows a preferred fluidized-bed reactor R which is configured as a circulating fluidized bed set-up comprising a riser RI, a cyclone Z, a bubble-forming fluidized bed as regenerator RI and a siphon S.

A phosgene-comprising gas stream 1 and a tolylenediamine-comprising stream 2 and also an inert stream of solid 8 are fed into the riser at the lower end thereof. The solid particle/reaction gas mixture, stream 3, is introduced from the upper end of the riser RI into the downstream cyclone Z. A product stream 4 is taken off from the cyclone Z via the overflow and the stream 5 comprising the circulating solid is taken off at the bottom. The stream 5 is introduced via a standpipe into a bubble-forming fluidized bed which functions as regenerator RE. An offgas stream, stream 6, is discharged from the upper region of the regenerator RE.

A stream 7 comprising the circulating inert solid is taken off from the regenerator RE in the lower region thereof and recycled as stream 8 via a siphon S to the lower region of the riser RI.

The standpipe and the siphon S are fluidized by means of inert gas, stream 9, and thus operated as strippers. The bubble-forming fluidized bed used as regenerator RE can likewise be operated using inert gas, stream 9, or else using air, stream 10, instead of inert gas. In the case of operation using air, carbon-comprising deposits on the solid particles are burnt off. The riser RI can likewise be supplied with inert gas to provide inertization and for aiding fluidization.

FIG. 3 shows a characteristic temperature profile in the riser RI, with the temperature T in ° C. being indicated on the abscissa and the height h of the riser RI in meters being shown on the ordinate.

EXAMPLES

The examples relate to a reactor corresponding to the schematic depiction in FIG. 2.

The plant pressure in the riser RI is 3 bar absolute, and the reaction temperature is 400° C.

The feed streams are set to 1.8 kg/h of tolylenediamine (stream 2) and 9 kg/h of phosgene (stream 1). The phosgene is introduced entirely in the gas phase, and the tolylenediamine is introduced entirely in the liquid phase.

Phosgene (stream 1) and tolylenediamine (stream 2) are introduced by means of two single-fluid nozzles into the lower region of the riser RI. As an alternative, phosgene (stream 1) and tolylenediamine (stream 2) can also be introduced by means of a two-fluid nozzle into the lower region of the riser RI. Nitrogen (stream 9) serves for fluidization. As an alternative, air can also be used for fluidization.

The inert solid particles used have a Sauter diameter of 65 μm and an apparent density, i.e. the average density of an inhomogeneous, porous particle based on its external geometric surface, of 1900 kg/m$^3$. The circulation rate is about 50 kg/m$^2$ on the basis of cold experiments.

Under the above conditions, the gas velocity in the riser RI is about 2 m/s and the residence time of the gas is accordingly 2 s.

The characteristic temperature profile in the riser RI for the above example is shown in FIG. 3.

The boiling point of tolylenediamine at 3 bar absolute is about 337° C. Under the extreme assumption that the vaporization of the tolylenediamine occurs before the reaction and 295 W are required for heating and vaporizing phosgene and tolylenediamine and a $c_p$ of the inert solid of 1.5 kJ/kgK is required, a local temperature decrease to at least 385° C. occurs. A constant temperature gradient of from 40 to 70° C. can therefore be assumed in the vaporization. The operation in the riser is vaporization-dominated in the lower region of the riser and is reaction-dominated in the upper region of the riser.

The energy balance for various temperatures is shown in the following table.

| Tolylenediamine | | Phosgene | | Heating and vaporization of tolylenediamine to target temperature Heating power [W] | Heating of phosgene to target temperature Heating power [W] | Heating power Total [W] | Heat of reaction [W] |
|---|---|---|---|---|---|---|---|
| $T_{in}$ [K] | $T_{out}$ [K] | $T_{in}$ [K] | $T_{out}$ [K] | | | | |
| 332 | 400 | 400 | 400 | 295 | 0 | 295 | 295 |
| 336 | 350 | 314 | 350 | 233 | 65 | 297 | 295 |
| 313 | 338 | 313 | 338 | 252 | 45 | 296 | 295 |

Surprisingly, the energy balance for the case of a preferred reaction temperature of 400° C. and liquid introduction of the tolylenediamine slightly below the vaporization temperature (about 5° C.) and preheating of the gas streams to reaction temperature is exact.

The invention claimed is:

1. A process for preparing an isocyanate, the process comprising:
   introducing a gas stream comprising phosgene into a fluidized-bed reactor, wherein the gas stream acts as a fluidizing gas and keeps an inert solid in suspension,
   feeding a liquid stream comprising an amine into the fluidized-bed reactor,
   vaporizing the amine partially or completely,
   reacting the amine with phosgene to obtain a reaction gas mixture comprising the isocyanate, and
   taking the reaction gas mixture from the fluidized-bed reactor.

2. The process according to claim 1, wherein the fluidized-bed reactor is a rotationally symmetrical apparatus having a vertical longitudinal axis.

3. The process according to claim 2, wherein the fluidized-bed reactor is a predominantly cylindrical apparatus.

4. The process according to claim 1, further comprising:
   before said introducing, heating the gas stream to a temperature which is at least 5° C. greater than a vaporization temperature of the amine under an operating pressure in the fluidized-bed reactor,
   wherein a content of phosgene in the gas stream is from 50 to 100% by weight, based on a total weight of the gas stream.

5. The process according to claim 1, further comprising:
   directly before said feeding, preheating the liquid stream to a temperature which is at least 1° C. below a boiling point of the amine under an operating condition in the fluidized-bed reactor,
   wherein a content of the amine in the liquid stream is from 50 to 100% by weight, based on a total weight of the liquid stream.

6. The process according to claim 1, wherein a mixture comprising the reaction gas mixture and the inert solid flows out of the fluidized-bed reactor in an upper region of the fluidized-bed reactor and is subject to a separation process.

7. The process according to claim 6, wherein the reaction gas mixture and the inert solid are separated during the separation process in one or more apparatuses selected from the group consisting of a cyclone and a filter.

8. The process according to claim 1, wherein from 50 to 100% of the amine have been reacted in the reaction gas mixture.

9. The process according to claim 1, further comprising:
feeding the reaction gas mixture to a subsequent residence time reactor to achieve complete reaction of the amine.

10. The process according to claim 1, further comprising:
cooling the reaction gas mixture in one or more stages by direct or indirect heat input, and
optionally condensing out a liquid phase during said cooling.

11. The process according to claim 1, wherein the inert solid is partly or completely recirculated to a lower part of the fluidized-bed reactor.

12. The process according to claim 1, wherein
the inert solid is worked up partly or completely to obtain a worked up solid, and
the worked up solid is partly or completely recycled to the fluidized-bed reactor.

13. The process according to claim 1, wherein the inert solid is a material inert toward all reactants and reaction products.

14. The process according to claim 1, wherein the inert solid has an average particle size of from 20 to 2000 μm.

15. The process according to claim 1, wherein the amine is a diamine.

16. The process according to claim 1, wherein at least one of the gas stream and the liquid stream is diluted with an inert component.

17. The process according to claim 1, wherein
said feeding occurs via one or more nozzles configured as single-fluid or two-fluid nozzles, and
when the two-fluid nozzles are used, an atomization gas is optionally a phosgene-comprising gas.

18. The process according to claim 17, wherein
when the two-fluid nozzles are used and the phosgene-comprising gas is the atomization gas, the two-fluid nozzles are optionally configured as externally mixing.

* * * * *

UNITED STATES PATENT AND TRADEMARK OFFICE
CERTIFICATE OF CORRECTION

Page 1 of 1

PATENT NO. : 8,791,291 B2
APPLICATION NO. : 13/687670
DATED : July 29, 2014
INVENTOR(S) : Torsten Mattke et al.

It is certified that error appears in the above-identified patent and that said Letters Patent is hereby corrected as shown below:

On the title page, Items (71) and (72), the 2nd Inventor's Last Name is incorrect. Items (71) and (72) should read:

--(71) Applicants: Torsten Mattke, Freinsheim (DE);
Carsten Knösche, Niederkirchen (DE);
Vanessa Simone Lehr, Mannheim (DE)--

--(72) Inventors: Torsten Mattke, Freinsheim (DE);
Carsten Knösche, Niederkirchen (DE);
Vanessa Simone Lehr, Mannheim (DE)--

Signed and Sealed this
Eighteenth Day of November, 2014

Michelle K. Lee
*Deputy Director of the United States Patent and Trademark Office*